(12) United States Patent
Tykocinski et al.

(10) Patent No.: US 7,569,663 B2
(45) Date of Patent: Aug. 4, 2009

(54) CHIMERIC PROTEINS AND METHODS FOR USING THE SAME

(75) Inventors: Mark L. Tykocinski, 300 Linden La., Merion Station, PA (US) 19066; Jui-Han Huang, Wallingford, PA (US)

(73) Assignee: Mark L. Tykocinski, Merion Station, PA (US)

( * ) Notice: Subject to any disclaimer, the term of this patent is extended or adjusted under 35 U.S.C. 154(b) by 190 days.

(21) Appl. No.: 10/169,686

(22) PCT Filed: Jan. 3, 2001

(86) PCT No.: PCT/US01/00145

§ 371 (c)(1),
(2), (4) Date: Oct. 31, 2002

(87) PCT Pub. No.: WO01/49318

PCT Pub. Date: Jul. 12, 2001

(65) Prior Publication Data

US 2003/0216546 A1 Nov. 20, 2003

Related U.S. Application Data

(60) Provisional application No. 60/174,258, filed on Jan. 3, 2000.

(51) Int. Cl.
*C07K 14/00* (2006.01)
*C07K 14/705* (2006.01)
*A61K 38/16* (2006.01)

(52) U.S. Cl. .............................. 530/350; 514/2; 514/12

(58) Field of Classification Search ........................ None
See application file for complete search history.

(56) References Cited

U.S. PATENT DOCUMENTS

| 5,851,795 | A | | 12/1998 | Linsley et al. |
| 5,916,560 | A | * | 6/1999 | Larsen et al. ............ 424/154.1 |
| 6,046,310 | A | | 4/2000 | Queen et al. |
| 6,632,789 | B1 | * | 10/2003 | June .............................. 514/1 |

| 2003/0035816 | A1 | * | 2/2003 | Peach et al. ............... 424/278.1 |
| 2003/0219863 | A1 | * | 11/2003 | Peach et al. ................. 435/69.1 |

OTHER PUBLICATIONS

Rudert et al., Biochem. Biophys. Res. Commun., 1994, 2004: 1102-1110.*
Timmer et al., J Pathol., 2002, 196: 125-134.*
Hollenbaugh et al., J. Immunol. Methods, 1995, 188: 1-7.*
Gessner et al., Ann. Hematol., 1998, 76: 231-248.*
Wong et al., 2000, Mol. Biol. Cell, 11: 3109-3121.*
Honda et al., 2003, Genes to Cells, 8: 481-491.*
Huang et al., 2001, International Immunol., 13: 529-539.*
Walczak et al., 1999, Nature Medicine, 5: 157-163.*
Ashkenazi et al., 1999, J. Clin. Invest., 104: 155-162.*
Gill et al., 1981, Horm. Metab. Res., 13: 603-609.*
Gibson et al., 1999, J. Biol. Chem., 274: 17612-17618.*
Jost et al., 2001, J. Invest. Dermatol., 116: 860-866.*
Wang et al., 2002, Mol. Cell, 9: 411-421.*
Greenwald et al., 2005, Annu. Rev. Immunol., 23: 515-548.*
Dranitzki-Elhalel et al., Cellular Immunol., 2006, 239: 129-135 (reference provided by Applicant).*
Lina Lu et al., "Blocking of the B7-CD28 Pathway Increases the Capacity of FasL (CD95L) Dendritic Cells to Kill Alloactivated T Cells", Dendritic Cells in Fundamental and Clinical Immunology, Plenum Press, New York, 1997.
Nobuhiko Kayagaki et al., "Polymorphism of Murine Fas Ligand that Affects The Biological Activity", Proc. Natl. Acad. Sci., vol. 94, pp. 3914-3919, Apr. 19, 1997.

* cited by examiner

*Primary Examiner*—Ilia Ouspenski
(74) *Attorney, Agent, or Firm*—Debra Z. Anderson; Meyer, Unkovic & Scott LLP

(57) ABSTRACT

Novel chimeric proteins are disclosed. The proteins comprise at least two portions. The first portion binds to a first cell and decreases the cell's ability to send a trans signal to a second cell; the second portion sends its own trans signal to the second cell. Methods for making and using these proteins in the treatment of cancer, viral infections, autoimmune and alloimmune diseases are also disclosed, as are pharmaceutical formulations comprising the novel chimeric proteins and genes. Either the proteins themselves or a genetic sequence encoding the protein can be administered. Other methods are also disclosed in which two molecular components result in decrement of a first trans signal from a first cell and the conferring of a second trans signal to a second cell.

3 Claims, 8 Drawing Sheets

SEQUENCE LISTING

```
<160> NUMBER OF SEQ ID NOS: 11

<210> SEQ ID NO 1
<211> LENGTH: 27
<212> TYPE: DNA
<213> ORGANISM: Homo sapiens

<400> SEQUENCE: 1
ttggggtacc atgtctcgct ccgtggc                                          27

<210> SEQ ID NO 2
<211> LENGTH: 35
<212> TYPE: DNA
<213> ORGANISM: Homo sapiens

<400> SEQUENCE: 2
aaaggatcca agctttccat gtctcgatcc cactt                                 35

<210> SEQ ID NO 3
<211> LENGTH: 25
<212> TYPE: DNA
<213> ORGANISM: Homo sapiens

<400> SEQUENCE: 3
atcaagcttg gagaagcaaa taggc                                            25

<210> SEQ ID NO 4
<211> LENGTH: 31
<212> TYPE: DNA
<213> ORGANISM: Homo sapiens

<400> SEQUENCE: 4
ttttggatcc ttagagctta tataagccga a                                     31

<210> SEQ ID NO 5
<211> LENGTH: 47
<212> TYPE: DNA
<213> ORGANISM: Homo sapiens
```

-continued

<400> SEQUENCE: 5
agcttaggtg gtggttctgg tggtggttct gactacaagg acgacga            47

<210> SEQ ID NO 6
<211> LENGTH: 48
<212> TYPE: DNA
<213> ORGANISM: Homo sapiens

<400> SEQUENCE: 6
agctacctcc tccagatcct cctcccttgt catcgtcgtc cttgtagt            48

<210> SEQ ID NO 7
<211> LENGTH: 24
<212> TYPE: PRT
<213> ORGANISM: Homo sapiens

<400> SEQUENCE: 7

Gly Gly Gly Ser Gly Gly Gly Ser Asp Tyr Lys Asp Asp Asp Lys
1               5                   10                  15

Gly Gly Gly Ser Gly Gly Gly Ser
            20

<210> SEQ ID NO 8
<211> LENGTH: 31
<212> TYPE: DNA
<213> ORGANISM: Homo sapiens

<400> SEQUENCE: 8
taaaaagctt gaaaccattt ctacagttca a                             31

<210> SEQ ID NO 9
<211> LENGTH: 31
<212> TYPE: DNA
<213> ORGANISM: Homo sapiens

<400> SEQUENCE: 9
taaaggatcc ggtcagttag ccaactaaaa a                             31

<210> SEQ ID NO 10
<211> LENGTH: 27
<212> TYPE: DNA
<213> ORGANISM: Homo sapiens

<400> SEQUENCE: 10
ttttggtacc atggcacggc cacatcc                                  27

<210> SEQ ID NO 11
<211> LENGTH: 27
<212> TYPE: DNA
<213> ORGANISM: Homo sapiens

<400> SEQUENCE: 11
gcacaagctt ctttggggtg gccagtg                                  27

CHIMERIC PROTEINS AND METHODS FOR USING THE SAME

CROSS REFERENCE TO RELATED APPLICATION

The present application claims priority to U.S. Provisional Application 60/174,258, filed Jan. 3, 2000.

This work was supported in part by Grants R01 CA-74958 and RO1 AI-31044 from the National Institutes of Health.

FIELD OF THE INVENTION

The present invention relates to novel chimeric proteins capable of attaching to a first cell and masking or otherwise interfering with a first signal from that cell, while also conferring a second type of signal to a second cell. The proteins are useful in the treatment of numerous immune disorders and other diseases. Methods for affecting a decrement in one cell and sending a trans signal to another cell are also disclosed.

BACKGROUND INFORMATION

There are two major arms to the immune system, supported by different types of cells called B-lymphocytes and T-lymphocytes (B-cells and T-cells). B cells make antibodies when they encounter antigens and, in most instances, these antibodies are protective. In autoimmune diseases, however, some of the antibodies react with the individual's tissues. When they deposit in tissue, they cause an inflammatory reaction and tissue damage. T-cells, like B-cells, are also activated when they encounter an antigen. As T-cells develop they undergo a process called "thymic education." During thymic education, more than 95% of the T-cells die. The T-cells that have had a T-cell receptor that can recognize and react with the individuals's own tissues (self-antigens) are specifically eliminated. Some autoreactive T-cells escape the elimination process, however, and can initiate an immune response that results in autoimmune disease.

The modulation of T-cell activity remains a significant therapeutic goal in diseases with immunopathological T-cells. The fate of T lymphocytes following T cell receptor (TCR) stimulation is guided by the integration of costimulatory and inhibitory receptor inputs. Costimulatory ligands on antigen-presenting cells (APC) trigger cognate receptor molecules on T cells, with resultant enhancement of T cell proliferation, cytokine secretion, and differentiation. In contrast, binding of inhibitory ligand molecules to cognate counter-receptors on T lymphocytes diminishes effector functioning by inducing T cell unresponsiveness or programmed cell death (PCD) (also referred to as apoptosis). Costimulatory and inhibitory receptor pathway interactions are suggested by experiments demonstrating increased inhibitor activity in the presence of costimulator blockade.

Cytotoxic T lymphocyte-associated protein-4 (CTLA-4 (CD152)) is an inhibitory receptor molecule that is expressed on the surface of activated T lymphocytes. Following engagement with the B7-1 (CD80) and/or B7-2 (CD86) ligands resident on APC, the CTLA-4 counter-receptor, via associated SHP-2 phosphatase, inhibits T cell activation. On activated T cells, CTLA-4 exists as disulfide-linked homodimeric glycoprotein complexes. A recombinant, soluble CTLA-4:immunoglobulin G (CTLA-4:Ig) chimeric protein demonstrates inhibitory function by competitively blocking CD80/CD86 molecule binding to the activating CD28 acceptor on T cell surfaces. CTLA-4:Ig also exhibits immunosuppressive activity in animal models of graft rejection and autoimmune disease by blocking T cell costimulation through CD28. In addition, intracellular T cell survival signaling through CD28 is antagonized by APC treatment with CTLA-4:Ig, which can increase susceptibility to Fas-dependent PCD. The action of CTLA-4, as well as CTLA-4:Ig fusion proteins, are discussed in U.S. Pat. Nos. 5,885,776; 5,885,579; 5,851,795; and 5,968,510.

Apoptosis (or PCD) is a distinct form of cell death which is essential for the regulation of cellular homeostasis. In the immune system, Fas (CD95) receptor and its ligand, FasL (CD95L), participate in various processes involved in the induction of apoptosis, including immune cell-mediated cytotoxicity, and in the regulation of cellular immune responses. FasL is a member of the tumor necrosis factor superfamily and is expressed by a restricted subset of immune cells, including monocytes, NK cells, and activated B and T cells. On the cell surface, FasL is oriented as a type II membrane protein within trimeric complexes. Metalloproteinase cleavage of membrane-associated FasL releases soluble FasL (sFasL) trimers from the membrane. The FasL molecule triggers Fas-dependent PCD.

The valency of a molecule or molecular complex can be increased by association with the cell surface. Different coding sequences of recombinant sFasL molecules affect macromolecular aggregation and, in turn, affect sFasL pro-apoptotic function. In particular, a naturally processed sFasL molecule forms trimers and poorly induces apoptosis. In contrast, a recombinant full-length extracellular domain sFasL polypeptide forms higher order aggregates and displays highly potent apoptotic activity. Furthermore, complexes of sFasL produced by recombinant expression in human 293 cells require cross-linking for lysis of Fas-sensitive cells.

U.S. Pat. No. 5,830,469 discloses monoclonal antibodies and binding proteins that specifically bind to human Fas antigen; some of the antigens and antibodies are reported as stimulating T cell proliferation, inhibiting of anti-Fas CH-11 monoclonal antibody-mediated lysis of cells, and blocking Fas ligand-mediated lysis of cells. Fas•Fc fusion proteins are also disclosed.

U.S. Pat. Nos. 5,242,687; 5,601,828; and 5,623,056 disclose various fusion proteins containing a CD8 component that bind to a cell but do not mask a signal produced by the cell.

U.S. Pat. No. 5,359,046 discloses chimeric proteins comprised of an extracellular domain capable of binding to a ligand in a non-MHC restricted manner, a transmembrane domain and a cytoplasmic domain capable of activating a signaling pathway. Similar technology is disclosed in U.S. Pat. No. 5,686,281.

While the art describes methods of transferring immunoregulatory molecules to cells, as well as various chimeric proteins, nothing in the art teaches use of proteins combining the two features of the present chimeric proteins. More specifically, no chimeric proteins reported in the art have been designed to function as both a blocking protein and a signaling protein. Indeed, nothing in the art teaches or even suggests such a result, or the desirability of such a result. These proteins have significant application in the treatment of immune system disorders and other diseases.

SUMMARY OF THE INVENTION

The present invention provides novel chimeric proteins that incorporate, by virtue of their component protein elements, three unique features: the capacity to bind to the surface of a first cell; the capacity to cause a decrement in a normal trans signal from the first cell; and the capacity to send a different trans signal to a second cell. Binding to the first cell serves to localize the chimeric protein to the cell. The chimeric protein can be designed to interfere with or "block" trans signals normally sent by the "anchor" molecule on the first cell. In addition, the chimeric protein can be designed to send its own trans signal to a second cell. Thus, the same chimeric protein can serve to block or mask or otherwise interfere with one type of signal while conferring a second type of signal. The present chimeric proteins can incorporate other useful features, such as epitope tags and/or other protein or non-protein elements that confer additional biological properties or therapeutic advantages, such as increased recombinant protein half-life in vivo, ease of purification through affinity chromatographic or other biochemical methods, and ease of protein detection ex vivo and in vivo through antibody-based or other binding elements. The chimeric proteins of the present invention can be configured in numerous ways to achieve the desired capabilities. For example, use of an inhibitory second protein renders the present proteins suitable for use in the treatment of immune system disorders, such as autoimmune and alloimmune diseases, whereas use of a stimulatory trans signaling element within the second protein component renders the present chimeric proteins suitable for treatment of illnesses in which immune cell stimulation is needed, such as cancer and infectious diseases.

The present invention further provides methods for making the present chimeric proteins, and methods for using these proteins in the study and treatment of autoimmune and alloimmune diseases. Other methods for studying and treating auto and alloimmune diseases are also disclosed. These methods have both in vivo and in vitro embodiments.

It is therefore an aspect of the invention to provide novel chimeric proteins that have the dual capability of both blocking one signal and sending another.

Another aspect of the present invention is to provide chimeric proteins for the study and treatment of autoimmune and alloimmune diseases and disorders, and the study and treatment of cancer and infectious diseases.

These and other aspects of the invention will be apparent based upon the following description and appended claims.

DETAILED DESCRIPTION OF THE INVENTION

Figure 1A:
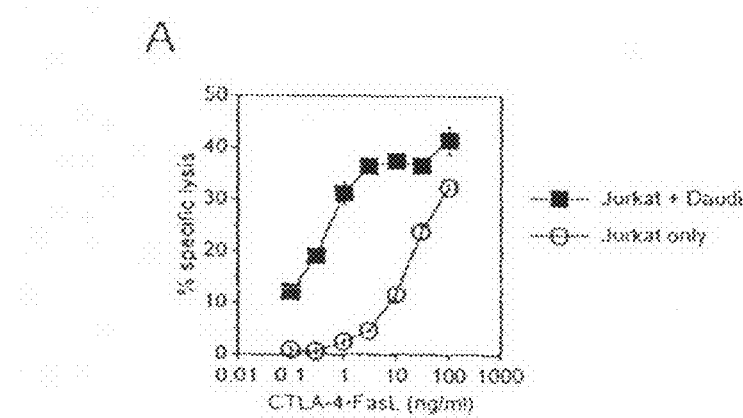
FIG. 1(A-D) demonstrates the cytotoxic activity of CTLA-4•FasL, the potentiation of CTLA-4•FasL activity by addition of CD80/CD86-expressing cells, the dependence of CTLA-4•FasL inhibitory activity of the FasL component of the chimeric protein, and CTLA-4•FasL's lack of requirement for antibody cross-linking (in contrast to B2M•FasL), determined according to Example 1.

The present invention is directed to a chimeric protein comprising a first protein that binds to a first cell, and through this binding functionally interferes with a signal emanating from this cell, and a second protein that sends a different signal to a second cell. The "interference" is a decrement in a trans signal normally transmitted by the first cell. In a preferred embodiment, the first protein is one that directly blocks or masks a signal sent by the first cell, also referred to herein as the "anchor" cell. The present chimeric proteins can be attached to the anchor cell in a quantitative manner. That is, the amount of chimeric protein that will bind to the anchor cells will be assessed by measuring the quantity of radioisotope-labeled, or otherwise labeled, chimeric protein bound to the anchor cells. The maximal quantity of chimeric protein binding to anchor cells will be dictated by the amount of the protein or other molecule that is resident on the anchor cells to which the chimeric protein binds.

The first protein can be selected so as to target a particular type or population of anchor cells. Similarly, the second protein can be selected so as to target a particular type or population of cells that receive a trans signal from the protein. A variety of surface molecules can be targeted on the first and second cells including proteins and glycolipids. The flexibility and utility of the present invention does not solely stem from the ability of chimeric proteins to target a diversity of different cell types. Since the surface molecular phenotype of individual cells can undergo changes with time, as a consequence of changes in their molecular and cellular milieu (dictating transitions in their metabolic, proliferative and/or differentiation states, for example), chimeric proteins can be designed that selectively bind to given first (anchor) and second cell types when they display specified surface molecular profiles. Hence, the chimeric proteins of the present invention can distinguish not only different cell types, but also the same cell type in different cell states, thereby combining temporal and spatial selectivities.

The present chimeric proteins can be configured in a number of ways to achieve a diversity of functional endpoints, depending on the needs and desires of the user. To this end, the chimeric proteins can be configured to contain more than two protein components. For example, the proteins can contain two or more trans signaling components, wherein each component is the same or different, and/or can contain epitope tags, and/or other protein or non-protein elements that confer special properties, such as increased stability, ease of purification through affinity chromatographic or other biochemical methods, ease of protein detection ex vivo and in vivo through antibody-based or other binding elements, ability to associate with other molecules through elements such as leucine zippers, and cleavaability with agents such as proteases. The first and second protein components of the chimeric proteins of the present invention can be derived from either type I or type II membrane proteins, that is, proteins whose amino termini are on either the extracellular or intracellular sides of the cell membrane. Additionally, the first and second protein components can be derived from proteins that are naturally soluble.

Any cells can be targeted as the anchor cell and the second cell receiving the trans-signal. Again, the first and second proteins can be configured to target the appropriate cell type for treatment of the particular illness or for the particular objective desired. For example, first cell/second cell combinations can include antigen presenting cells (APC)/T cells, T cells/T cells, T/cells/B cells, endothelial cells/hematopoietic cells, cancer cells/cancer cells, normal cells/cancer cells, cancer cells/normal cells, etc. It will be appreciated that this list is merely representative and not exhaustive of all of the potential first cell/second cell combinations.

Any suitable first protein can be used according to the present invention, provided the protein will bind to the surface of a cell, and through this binding event will lead to a decrement in a particular trans signal emanating from the cell. According to one embodiment of the present invention, the decrement in the trans signal results from the direct masking, or "competitive blocking", of those protein structural elements within the trans signaling protein of the anchor cell that normally contact the counter-receptor on the second cell, that is, the contact site. According to other embodiments of the present invention, the decrement in the trans signal can result from indirect mechanisms. This includes, but is not limited to, an embodiment in which the decrement in the trans signal can result from "allosteric inhibition" of the protein mediating the normal trans signal, with the first protein of the chimeric protein binding to a site on the trans signaling protein of the anchor cell that is distinct from the site or sites that directly contact the counter-receptor on the second cell. Since some natural trans signaling molecules are actually multi-molecular complexes, the first protein of the chimeric protein of the present invention can bind to one protein or other molecular component of the multi-molecular complex, and through this binding interfere with trans signaling from another molecular component of the complex, in another embodiment of the present invention. In yet another embodiment, the first protein of the chimeric protein of the present invention can trigger an intracellular signaling pathway within the anchor cell that results in the decrement of the trans signal. Thus, a unique feature of the first protein of the chimeric protein of the present invention is that it decreases or abrogates a natural trans signal by any one of a number of direct and/or indirect mechanisms, with examples including competitive blockade, allosteric inhibition, disruption of functional multi-molecular trans signaling complexes, and functional modification of the first signal via intracellular signaling.

First proteins can be chosen to cause a decrement in any one of a number of trans signals arising from a diversity of cell types or cells in different functional states. In one embodiment, the first protein blocks a costimulator on an APC surface. Preferred costimulator blockers include the costimulator receptor molecules CTLA-4, CD27 and ICOS. CTLA-4 is known to bind to, and thereby block, the B7 costimulators, including B7-1 (CD80) and B7-2 (CD86), of APC. CD27 binds to the costimulator CD70. ICOS binds to the costimulator B7-h. In another embodiment, the first protein blocks an inhibitory molecule on a cell surface. Preferred blockers of inhibitory molecules include Fas and DcR3, a naturally soluble analogue of Fas, which can interfere with the binding of the inhibitory Fas ligand to the Fas receptor on a second cell.

The first protein is not limited to soluble derivatives of native, cell surface counter-receptors for trans signaling molecules. Soluble cytokines can also be used as the first protein in the present chimeric proteins. Examples include, but are not limited to, tumor growth factor-beta (TGF-β), mullerian inhibiting substance (MIS), and hepatocyte growth factor (HGF). In this context, cytokines serve not only to direct the chimeric protein to the appropriate anchor cell (bearing the relevant cytokine receptor), but simultaneously trigger a signaling pathway within the anchor cell that alters its metabolic, proliferative, and/or differentiation state(s), along with its trans signaling repertoire. Hence, in one embodiment, the first protein is directed to a cytokine receptor on a cancer cell. TGF-beta receptors are preferred targets on cancer cells, since they are present on a variety of cancer cell types. On ovarian carcinomas, for example, TGF-beta receptors can trigger decreases in cellular proliferation. Yet another preferred target is hepatocyte growth factor receptors, which are found on breast and ovarian carcinomas, as well as malignant gliomas.

The single polypeptide chain derivative comprising the Fv region of an immunoglobulin molecule (scFv), for example of an immunoglobulin IgG1 molecule, can also be used as a first protein. Specific examples of scFv include ones with specificities for cytokine and other receptors (for example, HER-2/neu), carcinoembryonic antigen (CEA), prostate specific antigen (PSA), CD33 and AIRM1. HER-2/neu receptors are another preferred target on cancer cells, since they are found on epithelial carcinomas of the breast and ovary. CEA is highly expressed on gastrointestinal tumors, including colon cancer, and immunoinhibitory properties have been attributed to it. PSA is highly expressed by most epithelial prostate carcinomas. CD33 and AIRM1 are sialoadhesin family members expressed on cells of the myelomonocytic lineages. Ligation of CD33 or AIRM1 on chronic myeloid leukemia cells with antibodies decreases cell proliferation and survival.

Similarly, any suitable second protein can be used, provided the protein can send a signal to a second cell, i.e. a trans signal, that is distinct from the trans signal altered by the first protein component of the chimeric protein. The second protein can be a protein that sends an inhibitory signal, a protein that sends an activating signal, or a protein that alters any one of a large number of biological properties of the second cell, including its metabolic, proliferative, or differentiation state. A preferred example of an inhibitory protein is Fas Ligand (FasL). FasL is known to bind to, and thereby trigger, Fas receptors on activated T cells. Other examples of inhibitory proteins are TRAIL, TWEAK, CAR, CD40, CD8, PP14, BAFF/TALL-1/THANK/BLys, PD-1, and RCAS1. A preferred example of an activating protein is B7-1 (CD80), which can be used to deliver activating trans signals to T cells. Other examples of activating proteins are B7-2 (CD86), B7-h, CD40L (CD154), CD30L, OX-40L (CD134L), 4-1BBL (CD137L), CD70, ICAM-1, ICAM-2, ICAM-3, LFA-3 (CD58), HSA (CD24), LIGHT, SLAM, lymphotoxin, and any one of a large number of well-known chemokines. Examples of differentiation protein factors are TRANCE, c-KitL/SCF, IL-3, and GM-CSF. The examples cited are largely drawn from proteins relevant to the immune and hematopoietic systems, and thus represent but a small subset of the proteins that can be invoked as second proteins within the chimeric proteins of the present invention.

A preferred chimeric protein of the present invention is CTLA-4•FasL. Genetic chimerization of CTLA-4 with FasL sequences and recombinant expression results in chimeric CTLA-4•FasL "trans signal converter proteins" that demonstrate structural and functional characteristics attributable to both CTLA-4 and FasL. Comparison of the potency of soluble and cell-associated chimeric FasL polypeptides reveals significant augmentation of function following association with the cell surface. Cells pre-treated with CTLA-4-FasL acquire the competence to mediate Fas-dependent effector function. The function of pathogenic T cells can be eliminated by using CTLA-4•FasL chimeric proteins to simultaneously block B7 costimulation of T cells by APC, thereby interfering with a major cellular survival and activation pathway, and trigger Fas-mediated signaling in T cells, resulting in programmed cell death in some cases. CTLA-4•FasL thus provides a means for expressing FasL by exogenous delivery and for selectively coating CD80- or CD86-expressing cells within a mixed cell population. Moreover, the particular example of CTLA-4•FasL demonstrates that functional derivatives of type II membrane proteins (in this case FasL) are especially well-suited for the chimeric proteins of the present invention.

The present proteins can exist in numerous forms. For example, the present proteins can be in the form of a linear or branched polypeptide. Linear chimeric proteins can be produced by recombinant DNA technology. For example, chimeric transcription cassettes can be assembled using restriction endonuclease site overlap or the polymerase chain reaction (PCR)-based splice-by-overlap-extension (Horton, et al., *Gene,* 77:61-68 (1989)) methodologies. Specific methodologies are included in the examples below.

Branched polypeptide chimeric proteins can be readily produced by template-assembled synthetic peptide (TASP) technology (Mutter, *Trends Biochem. Sci.* 13:260-265 (1988)). By this process, the peptide units are synthesized separately and covalently coupled to a multifunctional carrier, such as a core peptide, using chemical coupling reagents. For example, a cyclic decapeptide analogue of gramicidin S, in which two antiparallel beta-sheet segments (lys-ala-lys) are linked by two beta-turns, can be used as a core peptide. Segment condensation strategies can be used to attach the first and second proteins to the epsilon-amino groups of the 4 lysine side chains.

The present proteins can also exist as two or more separate proteins linked together by a bridge, such as a chemical link. For example, two or more protein components can be covalently linked directly to each other in branched structures using chemical cross-linking reagents such as dithio-bis(succinimidyl proprionate) (DSP). By this methodology, for example, the first and second proteins can be directly linked. Branched, as opposed to linear, polypeptide, chimeric proteins are particularly well suited for lower affinity interactions, such as the binding of LFA-1 to ICAM-1, -2, and -3. Moreover, mixtures of trans signaling proteins can be applied simultaneously when incorporated into a branched polypeptide complex. In principle, synergistic effects generated by two or more trans signaling components are expected to increase the overall potency of the complex in some instances.

The present chimeric proteins, as noted above, can also contain one or more numerous other components that would enhance the utility of the present chimeric proteins, particularly in the areas of immunological study, animal models, diagnostics and therapeutics. For example, the proteins can be designed to contain an epitope tag. An epitope tag would be particularly useful in the laboratory setting to facilitate purification of the present proteins, to follow the localization of the proteins on cells or within populations of cells, and/or to enhance biological activity of the protein. For example, the primary sequence of either the first or second proteins can be altered through genetic engineering strategies to incorporate an epitope tag and thereby facilitate the biochemical isolation of the various proteins. A particularly useful alteration is the insertion of two or more neighboring histidine residues. This insertion can be in the amino or carboxy terminus of the peptide. The polyhistidine epitope tag could also be inserted into the linker peptide for the linear polypeptide chimeric proteins described above; for branched polypeptides the histidines can be inserted into the core peptide. Histidine residue insertion can be readily accomplished by the splice-by-overlap extension methodology, by incorporating histidine-encoding CAT and CAC triplet codons into the PCR primers at suitable locations in the coding sequence. Histidine-modified proteins can be efficiently and quantitatively isolated by the nickel-sepharose chromatography method. The histidine-nickel interaction is based upon protonation, and hence this interaction can be reversed, for purposes of peptide elution, through a simple pH shift. Other primary sequence modifications, such as the insertion of reactive amino acids for specific chemical coupling reagents, can also be performed. Alternatively, more conventional biochemical isolation strategies can be employed, including those based upon immunoaffinity. Other examples include the Flag epitope, which allows cross-linking of proteins, marker sequences and visualization sequences. For example, leucine zippers can be incorporated into the proteins in order to stabilize dimeric or trimeric complexes.

The present invention is also directed to methods for treating a patient for an illness comprising administering to the patient an effective amount of the chimeric proteins of the present invention. "Patient" refers to members of the animal kingdom, including but not limited to humans. With respect to immunomodulatory chimeric proteins, the present methods are generally applicable to patients capable of mounting at least a minimal immune response. Various illnesses can be treated according to the present methods, including but not limited to cancer, such as ovarian carcinoma, breast carcinoma, colon carcinoma, glioblastoma multiforme, prostate carcinoma and leukemia; viral infections, such as chronic viral infections with HBV, HCV, HTLV-1, HTLV-II, EBV, HSV-I, HSV-II, and KSHV; and autoimmune and alloimmune diseases, such as arthritis, asthma, graft-versus-host disease, organ rejection, psoriasis, systemic lupus erythematosis, atopic allergy, inflammatory bowel disease, multiple sclerosis, allergic dermatitis, Sjogren's syndrome, progressive systemic sclerosis, autoimmune thyroiditis, autoimmune diabetes, autoimmune liver diseases, and bone marrow myelodysplastic syndromes. "Illness" refers to any cancerous, viral, autoimmune or alloimmune condition.

The particular first and second proteins used in the methods will vary depending on the illness being treated. Typically, for example, when treating cancer or viral infections, second proteins that stimulate immune cell responses would be used. When treating immune system disorders where pathogenic immune responses exist, an inhibitory second protein would be used. Thus, for cancer and viral diseases, chimeric proteins will be used that typically convert inhibitory to activating immune trans activation signals. In the case of solid tumors, the tumor cells within the tumor bed will thus be converted into "immunogenic tumor cells" that can function as in situ-generated cancer vaccine cells. The immune-activating second protein component in this context can be directed to different anti-tumor immune effectors, including T cells (such as helper T cells and cytotoxic T cells), natural killer cells, and dendritic cells (that can function as bystander antigen-presenting cells to re-process and present tumor antigens). In contrast, for autoimmune and alloimmune diseases, chimeric proteins will be invoked that typically convert activating to inhibitory immune trans signals. In this setting, the immune-inhibitory second protein component can be directed to different pathogenic immune effectors, including T cells, B cells, natural killer cells, and antigen-presenting cells.

The chimeric proteins of the present invention can be used for therapeutic applications that go well beyond immunomodulation per se. For example, chimeric proteins can be used that modify signaling between endothelial cells and platelets for the treatment of thrombotic disorders; between bone marrow stromal cells/other marrow elements and hematopoietic progenitors, for the treatment of hematopoietic disorders such as bone marrow myelodysplastic syndromes; among tumor cells of a given tumor, for the induction of proliferative inhibition and/or cell death in these tumors cells and the like. Typically, for each disease application, a small "library" of candidate chimeric proteins will be generated and comparatively evaluated in appropriate and well-established ex vivo and in vivo models to determine relative efficacies and toxicities. For example, in the case of autoimmune diseases, the collection of chimeric proteins (or "trans signal convertor proteins") will comprise those with any one of a number of costimulator receptors (in soluble form) linked to any one of a number of T cell apoptosis inducers.

While a preferred method of the present invention involves administration of a therapeutic chimeric protein to a patient in need of said protein, an alternative treatment modality involves administration to said patient of a genetic sequence encoding the therapeutic chimeric protein of the present invention. "Genetic sequence" refers to a polynucleotide comprising the coding sequence for a defined protein and associated regulatory and other non-coding sequences. Genetic sequences in the form of cDNA clones are commercially available for a wide array of genes. Moreover, for those cDNA clones that are not readily accessible from commercial and other sources, knowledge of their nucleotide sequences can be used to easily reproduce their cDNAs via the reverse-transcriptase polymerase chain reaction method, incorporating the relevant gene sequences into the primers. This gene therapy approach is especially well-suited for patients requiring repeated administration of the therapeutic agent, since the exogenous genetic sequence can be incorporated into the patient's cells which will then produce the protein endogenously.

A broad array of methods for administering therapeutic genes to patients are well known in the art. These methods encompass a host of vectors for delivering therapeutic genes, a host of transcriptional and translational regulatory elements that can be appended to the gene of interest, methods for producing and using these vectors, methods for administering genes and vectors to patients, and methods for monitoring therapeutic gene efficacy and toxicity. A preferred embodiment involves intramuscular injection of a genetic sequence encoding a chimeric protein of the present invention. Once incorporated into the muscle cells of the patient, the encoded protein is produced and secreted systemically. The use of intramuscular gene therapy in this way for the treatment of autoimmunity is described in Chang, *J. Gene Medicine,* 1:415-423 (1999) and Piccirillo, *J. Immunology,* 161:3950-3956 (1998). An alternative embodiment involves local injection of the genetic sequence encoding a chimeric protein directly into a diseased site, for example, an inflammatory site, such as an inflamed joint. Lubberts, *J. Immunology,* 163:4546-4556 (1999) illustrates the direct intraarticular injection of a therapeutic gene into a knee joint in order to treat collagen-induced arthritis in an experimental animal. Significantly, inducible promoters are known in the art for regulating the expression of the transfected gene, so that levels of the encoded protein can be regulated. Those inducible promoters that can be regulated with orally-administered drugs are especially useful in this context. The genetic sequences of the present invention can be delivered to other organs, including liver, lung, and skin. Alternatively, the genetic sequences can be introduced into cells ex vivo by any one of a number of transfection modalities, and these transfected cells can be administered to a patient as therapeutic cells, according to methods well known in the art. The use of transfected cells as therapeutic cells in this way for the treatment of experimental osteoarthritis is described in Pelletier, *Arthritis and Rheumatism,* 40:1012-1019 (1997), wherein transfected synovial cells were re-injected back into diseased joints. This is also illustrated by Yasuda, *J. of Clinical Investigation,* 102:1807-1814 (1998) who described the treatment of autoimmune diabetes with transfected islet cells.

In yet another embodiment, a decrement in a trans signal coming from a first (anchor) cell and conferring a different trans signal to a second cell can be achieved using a combination of two or more chimeric or non-chimeric proteins that function in unison. In one preferred embodiment, a first chimeric protein binds to the first cell, and in so doing, effects a decrement in a first trans signal coming from the cell. A second chimeric protein binds to the first chimeric protein, and, once bound to the first chimeric protein on the first cell, confers the capacity to send a different trans signal to a second cell. In this embodiment, the first chimeric protein serves as a "beacon" attracting the second chimeric protein to a particular cell. The first chimeric protein is comprised of at least two functional moieties, one anchoring said protein to the first cell (and effecting a decrement in a first trans signal), and the other providing a site to which the second chimeric protein can bind in a specific fashion. The second chimeric protein is also comprised of at least two functional moieties, one directing said second chimeric protein to the cell surface-anchored first chimeric protein, and the other capable of sending a second trans signal to another cell.

The first and second chimeric proteins can be administered to a patient simultaneously (for example, as a molecular conjugate or as separate injected components) or sequentially, one at a time. It should be apparent that the critical functional components of the first and second chimeric proteins can be selected from those detailed for the first and second protein components of the chimeric protein discussed above. The additional components of each of the chimeric proteins are paired recognition units that link the first and second chimeric proteins. Such recognition units can be drawn from a diverse set of paired recognition units well known in the art, for example, an epitope tag and a scFv with specificity for the tag, self-associating leucine zippers, and the like.

In yet another embodiment, the two functions of effecting a decrement in a first trans signal and providing a second trans signal are achieved using two or more distinct proteins that do not directly interact with each other, but rather each independently bind to the first cell. At least one of the proteins would have the ability to mask or otherwise interfere with a signal from the anchor cell, and at least one of the proteins would have the ability to send a trans signal to a second cell. Again, any of the first and second protein components discussed above can be used as the proteins in this embodiment.

The present invention is therefore also directed to therapeutic methods comprising the administration to a patient of two or more molecular components that together effect a decrement in a first trans signal from a first cell and confer a second trans signal from said first cell. "Molecular components" refers to both chimeric proteins and non-chimeric proteins. As discussed above, when the molecular components are both chimeric proteins, the first will bind to the anchor cell and the second will bind to the first. When the molecular components are non-chimeric proteins they do not bind to each other, but rather each bind directly to the anchor cell.

Examples of various chimeric proteins and the illness and clinical syndromes treated by each protein are provided below. It will be understood that this list is not exhaustive, but rather is merely a small sample of the types of chimeric proteins and illnesses that can be treated according to the present invention.

| Chimeric protein | Disease Category |
|---|---|
| CTLA-4·FasL | Autoimmune and alloimmune diseases |
| CTLA-4·TRAIL | Autoimmune and alloimmune diseases |
| CTLA-4·TWEAK | Autoimmune and alloimmune diseases |
| CD27·TRAIL | Autoimmune and alloimmune diseases |
| CD27·TWEAK | Autoimmune and alloimmune diseases |
| ICOS·TRAIL | Autoimmune and alloimmune diseases |
| ICOS·TWEAK | Autoimmune and alloimmune diseases |
| Fas·c-kit | Bone marrow myelodyeplastic syndromes |
| Fas·GM-CSF | Bone marrow myelodyeplastic syndromes |
| Fas·IL-3 | Bone marrow myelodyeplastic syndromes |
| DcR3·c-kit | Bone marrow myelodyeplastic syndromes |
| DcR3·GM-CSF | Bone marrow myelodyeplastic syndromes |
| DcR3·IL-3 | Bone marrow myelodyeplastic syndromes |
| TGF-β·FasL | Gynecological and other malignancies |
| TGF-β·TRAIL | Gynecological and other malignancies |
| MIS·4-1BB ligand | Genitourinary malignancy |
| MIS·OX-40 ligand | Genitourinary malignancy |
| MIS·CD40 ligand | Genitourinary malignancy |
| MIS·CD70 | Genitourinary malignancy |
| HGF·FasL | Breast/Central nervous system malignancy |
| HGF·TRAIL | Breast/Central nervous system malignancy |
| scFv(HER-2/neu)·4-1BB ligand | Gynecological and other malignancies |
| scFv(HER-2/neu)·OX-40 ligand | Gynecological and other malignancies |
| scFv(HER-2/neu)·CD40 ligand | Gynecological and other malignancies |
| scFv(HER-2/neu)·CD70 | Gynecological and other malignancies |
| scFv(HER-2/neu)·TRANCE | Gynecological and other malignancies |
| scFv(HER-2/neu)·TRAIL | Gynecological and other malignancies |
| scFv(HER-2/neu)·FasL | Gynecological and other malignancies |
| scFv(HER-2/neu)·TWEAK | Gynecological and other malignancies |
| scFv(CEA)·4-1BB ligand | Gastrointestinal malignancy |
| scFv(CEA)·OX-40 ligand | Gastrointestinal malignancy |
| scFv(CEA)·CD40 ligand | Gastrointestinal malignancy |
| scFv(CEA)·CD70 | Gastrointestinal malignancy |
| scFv(CEA)·TRANCE | Gastrointestinal malignancy |
| scFv(CEA)·TRAIL | Gastrointestinal malignancy |
| scFv(CEA)·FasL | Gastrointestinal malignancy |
| scFv(CEA)·TWEAK | Gastrointestinal malignancy |
| scFv(PSA)·4-1BB ligand | Genitourinary malignancy |
| scFv(PSA)·OX-40 ligand | Genitourinary malignancy |
| scFv(PSA)·CD40 ligand | Genitourinary malignancy |
| scFv(PSA)·CD70 | Genitourinary malignancy |
| scFv(PSA)·TRANCE | Genitourinary malignancy |
| scFv(PSA)·TRAIL | Genitourinary malignancy |
| scFv(PSA)·FasL | Genitourinary malignancy |
| scFv(PSA)·TWEAK | Genitourinary malignancy |
| scFv(CD33 or AIRM1)·4-1BB ligand | Hematological malignancy |
| scFv(CD33 or AIRM1)·OX-40 ligand | Hematological malignancy |
| scFv(CD33 or AIRM1)·CD40 ligand | Hematological malignancy |
| scFv(CD33 or AIRM1)·CD70 | Hematological malignancy |
| scFv(CD33 or AIRM1)·TRANCE | Hematological malignancy |
| scFv(CD33 or AIRM1)·TRAIL | Hematological malignancy |
| scFv(CD33 or AIRM1)·FasL | Hematological malignancy |

As noted above, an effective amount of the present proteins should be used in the treatment of a patient. Similarly, genetic sequence encoding the present proteins should be administered in an amount sufficient to generate an effective amount of the protein. As used herein, the term "effective amount" refers to that amount of the chimeric proteins, delivered in one or more doses, necessary to bring about the desired result in the patient. Generally, the desired result will be, for example, stimulation of an immune response or suppression of an immune response, depending on the illness being treated. In the case of cancer treatment, for example, an effective amount would be that amount which would protect a patient against tumor growth or reduction, if not elimination, of tumors. In the case of the treatment of autoimmune, alloimmune or a viral disease, an effective amount would be that amount which would alleviate, if not eliminate, one or more symptoms of the disease being treated. Accordingly, the "effective amount" can be a therapeutically effective amount, useful for treating someone already afflicted with the illness, or can be a prophylactically effective amount useful for prevention, spread or recurrence of an illness in a patient. It will be appreciated that the effective amount will vary from patient to patient depending on such factors as the illness being treated, the severity of the illness, the size of the patient being treated, the patient's ability to mount an immune response, and the like. The determination of an effective amount for a given patient is within the skill of one practicing in the art. Typically, an effective amount will be determined by evaluating potency in standard ex vivo cellular systems, followed by preclinical and clinical in vivo assessment and will be between about 0.005 and 0.5 mg/kg body weight.

Administration can be by any means known in the art, such as by injection. The chimeric or non-chimeric proteins or a gene sequence encoding the same as described herein can be contained within a suitable pharmaceutical carrier for administration according to the present methods. "Suitable pharmaceutical carrier" includes any and all solvents, dispersion media, coatings, antibacterial and antifungal agents, isotonic and absorption delaying agents, and the like. The use of such media and agents for pharmaceutical use is well-known in the art. Use of any of these media or agents is contemplated by the present invention, absent compatability problems with the chimeric proteins. A saline solution is a suitable carrier.

It is especially advantageous to formulate parenteral compositions in dosage unit form for ease of administration and uniformity of dosage. Dosage unit form as used herein refers to physically discrete units suited as unitary dosages for the patients being treated, each unit containing a predetermined quantity of chimeric protein or a gene sequence encoding the same, or effective amount of chimeric protein or a gene sequence encoding the same, to produce the desired effect in association with the pharmaceutical carrier. The specification for the dosage unit forms of the invention are dictated by and directly dependent on the particular chimeric protein and the particular effect to be achieved by the protein.

The present invention is also directed to a method for producing an animal model for the study of the illnesses disclosed herein. For example, there are a growing set of animal autoimmune disease models that can be used in conjunction with the chimeric proteins of the present invention. These animal models include ones in which the autoimmunity arises spontaneously as a result of genetic mutations that arose spontaneously (for example diabetic NOD mice) or were introduced via transgenesis, and other animal models in which autoimmunity is induced artificially through the introduction of a pathogenic agent.

EXAMPLES

The following examples are intended to illustrate the present invention and should not be construed as limiting the invention in any way.

Example 1

Plasmid Construction and Transfection

Two targeting domains were genetically chimerized with sequences encoding soluble FasL: extracellular domain sequence from human CTLA-4 and human beta-2-microglobulin (B2M). The chimerization of FasL with CTLA-4 within CTLA-4•FasL allows binding to resident B7-1/B7-2 (CD80/CD86) molecules on APC, in addition to the pro-apoptotic activity of FasL. The soluble B2M•FasL protein was developed as a control. For expression of chimeric sFasL-containing proteins, recombinant expression plasmids were constructed and expressing cell lines selected from transfected 293 human embryonic kidney cells.

The cDNAs for human FasL have been described previously by Takahashi (1994). Synthetic oligonucleotides were purchased from Genosys, Inc. (The Woodlands, Tex.). DNA primers were designed to replace the stop codon of human B2M with a HindIII restriction site. DNA primers for the generation of a human B2M sequence encoding amino acids −20 to 99 of B2M were 5'-TTGGGGTACCATGTCTCGCTCCGTGGC-3' (SEQ ID NO: 1) and 5'-AAAGGATCCAAGCTTTCCATGTCTCGATCCCACTT-3' SEQ ID NO: 2). PCR was performed with Pfu DNA polymerase according to the manufacturer's specifications (Stratagene, La Jolla, Calif.), using pB2M/REP12β (provided by H. Meyerson, University Hospitals of Cleveland) as a DNA template. Following purification and enzymatic restriction, the 360 bp Kpn I-HindIII DNA fragment was subcloned into the respective sites of the episomal expression vector pCEP9β (Invitrogen, LaJolla, Calif.), generating pB2MX/CEP9β. DNA primers allowing for the amplification of sequences encoding amino acids 127 to 281 of human FasL were 5'-ATCAAGCTTGGAGAAGCAAATAGGC-3' (SEQ ID NO: 3) and 5'-TTTTGGATCCTTAGAGCTTATATAAGCCGAA-3' (SEQ ID NO: 4). Following purification and enzymatic digestion, the 480 bp HindIII-BamHI DNA fragment was subcloned into the respective sites of pB2MX/CEP9β and pCEP9β, generating pB2M•FasL/CEP9β and pXFasL/CEP9β, respectively. Partially overlapping synthetic oligonucleotides 5'AGCTTAGGTGGTGGTTCTGGTGGTGGTTCTGACTACAAGGACGACGA-3' (SEQ ID NO: 5) and 5'-AGCTACCTCCTCCAGATCCTCCTCCCTTGTCATCGTCGTCCTTGTAGT-3' (SEQ ID NO: 6), together encoding the Flag epitope tag flanked by a linker sequence $(GGGS)_2$DYKDDDDK$(GGGS)_2$ (SEQ ID NO: 7), were subcloned into the HindIII site of pB2M•FasL/CEP9β, yielding pB2M•Flag-FasL/CEP9β. All constructs were confirmed by sequencing. pCTLA-4•FasL/CEP9β was generated by replacing the stuffer fragment sequences in pXFasL/CEP9β with the HindIII insert encoding the oncostatin M signal sequence and human CTLA-4 extracellular sequences mobilized from phCTLA-4:IgG1/REP7β, according to the method described by Brunschwig, (1995). Transfectant cell lines were generated by introduction of episomal expression plasmids into 293 cells with LIPOFECTIN™ transfection reagent (Life Technologies, Bethesda, Md.). Selection of stable cell lines was performed in D10 medium supplemented with G418 (Life Technologies, Bethesda, Md.) 0.4 mg per mL, for transfectant cell lines containing pCTLA-4FasL/CEP9β, pB2M•Flag-FasL/CEP9β, or pB2M/REP12β. Multiple individual colonies were picked and screened for recombinant polypeptide expression. Secretion of the recombinant sFasL-containing proteins by transfectant cell lines was quantitated by commercial soluble FasL ELISA (MBL, Cambridge, Mass.) and ranged from 100-1000 ng/mL.

Cell culture

Cell lines obtained from the ATCC (Bethesda, Md.) included Jurkat transformed human T cells, 293 human embryonic kidney cells, and Raji and Daudi EBV-transformed B cell lines. The EBV-transformed B cell line, JY, was provided by Francis V. Chisari (Scripps Institute). All cells were maintained in humidified incubators providing 5% $CO_2$ RPMI-1640 and high glucose DMEM media, antibiotics, glutamine, and fetal bovine serum (FBS) were obtained from Bio Whittaker (Bethesda, Md.). Jurkat cells were cultured in RPMI-1640 supplemented with 100 μg/ml penicillin, 100 U/mL streptomycin, 2 mM glutamine, and 10% heat-inactivated FBS (R10). 293 cells were cultured in DMEM supplemented with 100 μg/ml penicillin/streptomycin, 2 mM glutamine, and 10% heat inactivated FBS (D10). Conditioned media were prepared by culturing cells for 5-6 days in CELLGRO™ Free cell culture media containing penicillin/streptomycin and L-glutamine (Mediatech). Cellular debris was removed from cell culture supernatants by centrifugation (6 minutes at 400×g) followed by filtration through 22 micron sterile syringe filters. Clarified supernatants were stored at 4° C. for two months without significant loss of activity. A commercial sFasL ELISA (MBL, Cambridge, Mass.) was used to quantitate sFasL-containing proteins in samples.

Western Blotting and Gel Filtration Chromatography

Both FasL and CTLA-4 molecules, in their natural forms, form multimeric complexes. Natural FasL exists as a non-covalently-associated homotrimer, and CTLA-4 exists as a disulfide-linked homodimer. To determine if CTLA-4•FasL forms multimeric complexes, immunoblotting experiments were performed. Supernatant samples from two CTLA-4•FasL transfectant cell line clones were prepared in the presence or absence of reducing agent (2-mercaptoethanol), boiled, and subjected to SDS gel electrophoresis and immunoblotted using FasL-specific antiserum.

More specifically, clarified cell culture supernatants were concentrated 15-30 fold with CENTRICON™-10 ultrafiltration devices (Amicon, Beverly, Mass.). Concentrated CTLA-4•FasL samples were applied to a pre-calibrated SUPERDEX™-200 column in 1×PBS. 0.5 mL fractions were collected and functionally analyzed using a cytotoxicity assay. Fractions containing active CTLA-4•FasL molecules were concentrated 50-fold and then co-incubated with the chemical cross-linker dithiobis[succinimidyl proprionate] (DSP, Pierce) at room temperature for 30 minutes prior to quenching with 1 M Tris, pH 7.5. Samples for SDS-PAGE analysis were prepared in Laemmli sample buffer with or without 2-mercaptoethanol and boiled prior to loading onto 10% acrylamide SDS-PAGE gels. Following electrophoresis, gels were blotted onto IMMOBIILON™ P membranes (Millipore, Beverly, Mass.), blocked with 5% milk/PBS and probed with anti-human FasL antiserum (anti-C20, Santa Cruz Biologicals). After extensive washing, blots were incubated with horseradish peroxidase (HRP)-conjugated anti-rabbit antiserum (BioRad, Richmond) and developed with enhanced chemiluminescent substrate (New England Nuclear, Boston, Mass.) prior to exposure to X-ray film.

A weak band at ~45 kDa and a stronger band at 70-90 kDa were observed with the samples derived from the CTLA-4•FasL clones in the absence of reducing agent. Addition of reducing agent caused the disappearance of the 70-90 kDa molecular species and an increase in the ~45 kDa species. No significant FasL immunoreactivity was seen with the control 293 cell supernatant sample.

To determine the molecular stoichiometry of CTLA-4•FasL complexes, proteins in the transfectant cell conditioned media were cross-linked with the homobifunctional, reducible cross-linker DSP and analyzed by immunoblotting using FasL-specific antiserum. More specifically, supernatant samples containing CTLA-4•FasL were pre-incubated at room temperature for 30 minutes with solvent alone or DSP dissolved in DMSO. Reactions were quenched with 1 M Tris, pH 7.5; samples were processed for SDS-gel electrophoresis and immunoblotting was as described above. Immunodetection of high molecular weight 90 kDa and ~180-200 kDa CTLA-4-FasL molecular species increased following DSP cross-linking. Partial reduction of cross-linked CTLA-4•FasL complexes revealed a band of ~45 kDa, as well as bands consistent with dimeric complexes (~90 kDa) and trimeric complexes (~180-200 kDa). In similar chemical cross-linking experiments, the ~40 kDa B2M•FasL monomer was also shown to form trimeric complexes of ~120 kDa. Gel filtration chromatography was also performed as an independent method to measure the molecular weight of the CTLA-4•FasL trimeric complexes. Peak column fractions, as determined by solid phase assay, eluted at ~180-220 kDa. Chemical cross-linking of peak fractions followed by anti-FasL immunoblotting also revealed the 90 kDa and 180-200 kDa CTLA-419 FasL complexes. The chemical cross-linking and gel filtration analyses, taken together, show that CTLA-4•FasL complexes contain intermolecular disulfide-bridges and indicate a trimeric molecular stoichiometry.

Flow Cytometry

Cells were pre-incubated with various dilutions of cell culture supernatants containing either B2M•FasL or CTLA-4•FasL on ice for 30 minutes. Cells were pelleted and washed twice with FACS buffer (1×PBS/0.5% BSA/0.02% sodium azide) and incubated on ice for 30-45 minutes with 10 µg per mL of primary antibody. Antibody specific for human FasL (CD95L, clone NOK-1) was purchased from Pharmingen (La Jolla, Calif.). Mouse IgG1 (Dako) was used as a control. Cells were then incubated on ice for 30-45 minutes with FITC-conjugated goat F(ab')2 anti-mouse IgG (Boerhinger Mannheim). Following washes, fluorescence-labeled cells were run on a FACScan, and propidium iodide-excluding populations were gated for analysis with the LYSIS™ II software package (Becton-Dickinson, Mountain View, Calif.). Cytotoxicity assay to determine apoptotic activity of the CTLA-4•FasL and B2M•FasL chimeric proteins.

To determine whether CTLA-4•FasL and B2M•FasL proteins display agonist functioning, protein-containing cell culture supernatants were tested for the induction of apoptosis of Fas-sensitive Jurkat T cells. Apoptosis was measured by a radiometric DNA fragmentation assay.

Assays were performed in triplicate, as described by Matzinger (1991) with a few modifications. Jurkat cells in exponential growth phase were labeled at 37° C. for 4 to 5 hours with 3 microcuries of $^3$H-thymidine (ICN, Costa Mesa, Calif.) per mL of R10 medium, pelleted, and washed twice. Cells were resuspended at $2\times10^5$/mL, and 0.1 mL of this cell suspension was added to each well. Clarified supernatants containing CTLA-4•FasL or B2M•FasL were diluted into R10, and 0.1 mL of these supernatants was added per well to round bottom 96 well tissue culture plates. Anti-Flag antibody was added as cross-linker at 0.5 micrograms per mL to indicated samples. Pre-incubation of cells with defined quantities of CTLA-4•FasL or B2M•FasL was performed on ice for one hour, followed by centrifugation (6 minutes at 400×g) and two washes with R10. For cell-cell killing assays, $10^4$ pre-treated effector cells were added per well. Cultures were incubated overnight at 37° C., and radiolabeled DNA was harvested onto glass filters for scintillation counting. In blocking experiments, antibodies were either pre-incubated with Jurkat cells (anti-Fas, clone ZB4, Coulter Immunotech) or with chimeric protein-containing supernatants (anti-FasL). Percent Fas-dependent specific lysis=100×{(spontaneous release—experimental)/(spontaneous release)}. Maximal killing ranged from 40-70% depending on the assay. Soluble CTLA-4•FasL proteins display low potency cytotoxicity against Jurkat cells, which is potentiated by co-incubation with CD80/CD86 positive Daudi cells (FIG. 1A). Supernatants containing known quantities of CTLA-4•FasL proteins, as indicated on the x-axis of FIG. 1A, were titrated into wells. Absence or presence of added Daudi cells are indicated by open circles and filled squares, respectively, in FIG. 1A. As can be seen in the figure, CTLA-4•FasL displays dose-dependent killing of Jurkat cells from 1-100 ng/ml.

Figure 1B:
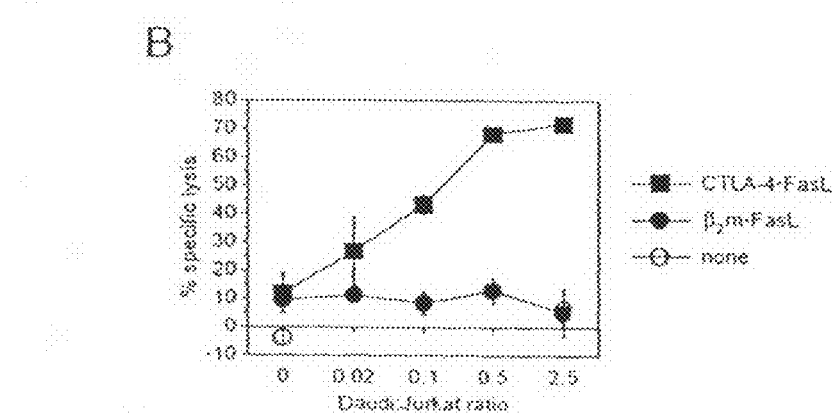

Addition of Daudi Burkitt's lymphoma B cells, which constitutively express moderate levels of CD80 and high levels of CD86, lowered the limit of detection of apoptosis to 0.1 ng/mL of CTLA-4•FasL, thereby potentiating CTLA-4•FasL cytotoxic activity by approximately 60-fold. Two other EBV-transformed B cell lines, JY and Raji, with CD80 and CD86 expression profiles similar to Daudi cells, also potentiated cytotoxicity by CTLA-4•FasL molecules, but not B2M•FasL (data not shown). Increasing numbers of Daudi cells added with CTLA-4•FasL increased cytotoxic activity. In addition, titration of the number of Daudi cells added to wells revealed a dose-dependent increase in Jurkat cell death (FIG. 1B). The ratio of added Daudi cells to Jurkat cells is indicated on the x-axis; symbols representing CTLA-4•FasL at 0.6 ng/ml (filled squares) and B2M•FasL at 1 ng/mL (filled circles), or medium alone (open circles) are indicated in the FIG. 1B legend.

Figure 1C:
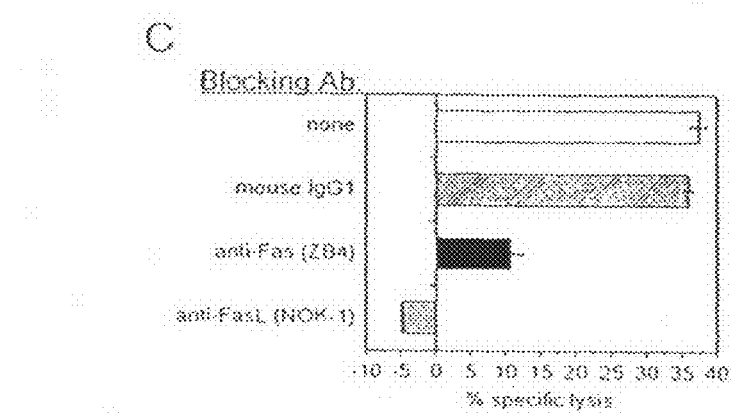

Inhibition of CTLA-4•FasL cytotoxicity by Fas- and FasL-antagonistic monoclonal antibodies is shown in FIG. 1C. CTLA-4•FasL was preincubated with FasL-specific antibody (anti-FasL (NOK-1) or isotype-matched control antibody (Leu2a), at 10 micrograms per ml for 1 hour at 37° C., prior to the addition of radiolabeled Jurkat cells. For anti-Fas blocking, the antagonistic antibody ZB4 was pre-incubated with radiolabeled Jurkat cells prior to co-culture in the presence of CTLA-4•FasL at 2 ng/ml. Grey, black and hatched bars represent anti-FasL, anti-Fas and control antibodies, respectively, with the white bar representing no added antibody. As shown, CTLA-4•FasL-mediated cytotoxicity is sensitive to anti-FasL and anti-Fas monoclonal antibody blockade, consistent with a requirement for FasL and Fas for Jurkat cell apoptosis by this chimeric protein (FIG. 1C).

Figure 1D:
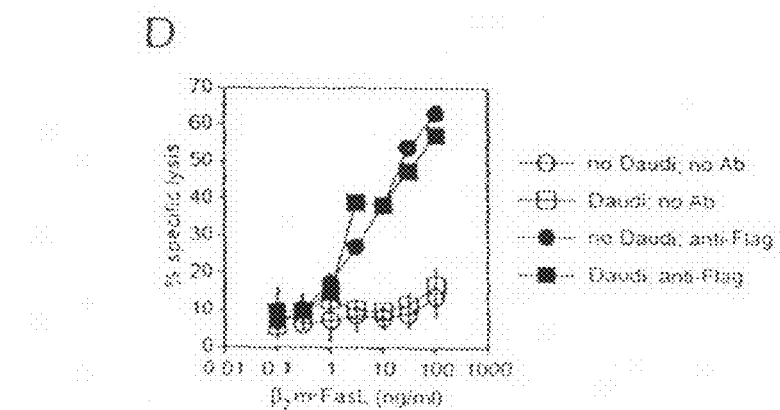

B2M•FasL requires cross-linking for cytolysis of Jurkat cells, as confirmed in FIG. 1D. As indicated on the x-axis, B2M•FasL was titrated into wells for assessment of Jurkat cell cytotoxicity. After 16-20 hours at 37° C., cultures were harvested onto fiberglass filters for scintillation counting and percent specific lysis was calculated, as displayed on the y-axis. Samples incubated in the presence of B2M•FasL plus anti-Flag, B2M•FasL plus Daudi cells, or B2M•FasL alone are represented by the symbols filled circles, open squares, and open circles, respectively. Error bars represent 1 standard deviation. As shown, no significant killing of Jurkat cells is detected with B2M•FasL alone over the range 0.1 to 100 ng/mL, except in the presence of a cross-linking epitope-tagged specific antibody. Hence, CD80/CD86-positive cells potentiate the ability of CTLA-4•FasL molecules to signal through Fas receptors in trans on Jurkat cells.

Example 2

Role of Cell-to-Cell Contact in Mediating CTLA-4•FasL Trans-effector Activity

Figure 2A:
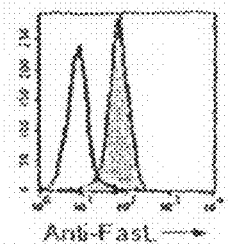
FIG. 2(A-C) demonstrates that cells pretreated with CTLA-4•FasL acquire the ability to trigger cytotoxicity of Fas-sensitive cells, in a cell contact-dependent fashion, determined according to Example 2.
Figure 2A:
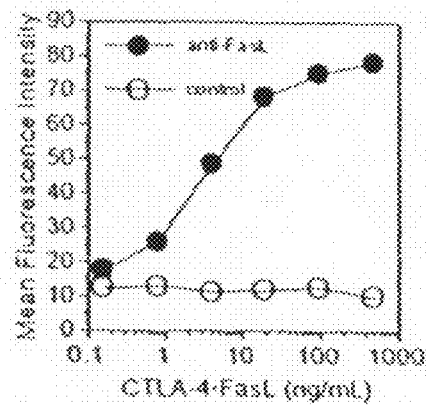

Soluble CTLA-4 polypeptide derivatives, such as CTLA-4•Ig, bind to cells expressing CD80 and/or CD86. To test whether the binding of CTLA-4•FasL molecules to CD80/CD86-positive cells potentiate Jurkat cell apoptosis, the ability of CTLA-4•FasL to bind Daudi and Jurkat cells was assessed. CD80/CD86-positive Daudi cells were pre-incubated with CTLA-4•FasL-containing cell supernatants and processed for indirect immunofluorescence and flow cytometry using a FasL-specific monoclonal antibody or an isotype-matched control antibody. More specifically, pre-incubation was performed at 0° C. for 30-45 minutes. After two washes, cells were incubated with anti-FasL antibody (NOK-1, J) or isotype-matched control antibody (Control, E) at 10 mg/ml for 30-45 minutes at 37° C. Following two washes, cells were incubated with FITC-conjugated goat anti-mouse IgG. After washes, data acquisition was performed on a FACScan flow cytometer and data analyzed with CELLQUEST software. Mean fluorescent intensities are plotted on the y-axis for each CTLA-4•FasL concentration, as indicated on the x-axis in FIG. 2A. Dose-dependent increases in cell surface FasL were observed following pre-treatment with increasing amounts of CTLA-4•FasL (FIG. 2A, upper panel) and staining was saturated at ~100 ng/mL. A similar analysis of CTLA-4•FasL binding to Fas on Jurkat cells revealed dose-dependent increases in CTLA-4 epitopes from 30-300 ng/mL (FIG. 2A, lower panel). These results are consistent with the dual binding activities of CTLA-4•FasL; the CTLA-4 moiety binds CD80/CD86 molecules and the FasL domain binds to Fas receptors.

Figure 2B:
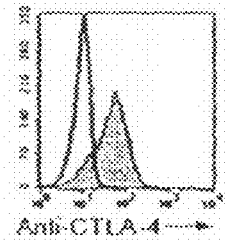
Figure 2B:
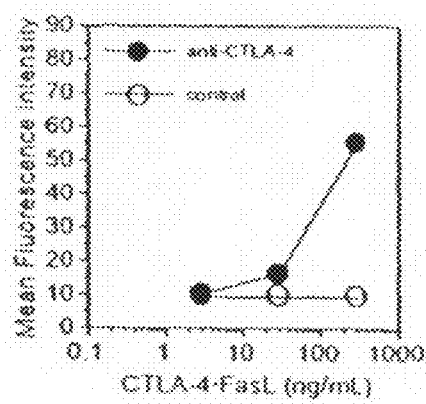
Figure 2B:
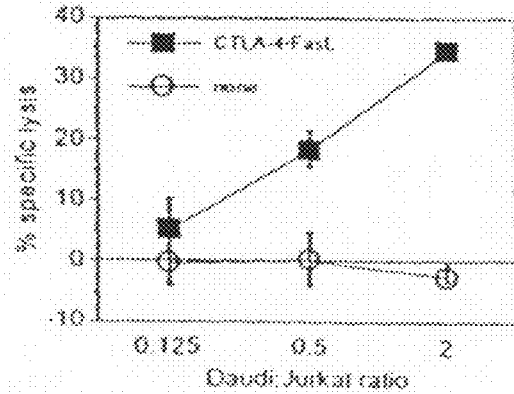

Daudi cells were pre-incubated with medium alone or CTLA-4•FasL at 37° C. for 1 hour. Following three washes, cells were counted and plated into wells for radiometric DNA fragmentation assay. Percent specific lysis results are plotted on the x-axis. When tested in functional assays, CTLA-4•FasL-pre-treated Daudi cells induced dose-dependent Jurkat cell PCD compared to untreated Daudi cells (FIG. 2B). Pre-incubation of Daudi cells with B2M•FasL resulted in no significant Jurkat cell cytolysis (data not shown).

Figure 2C:
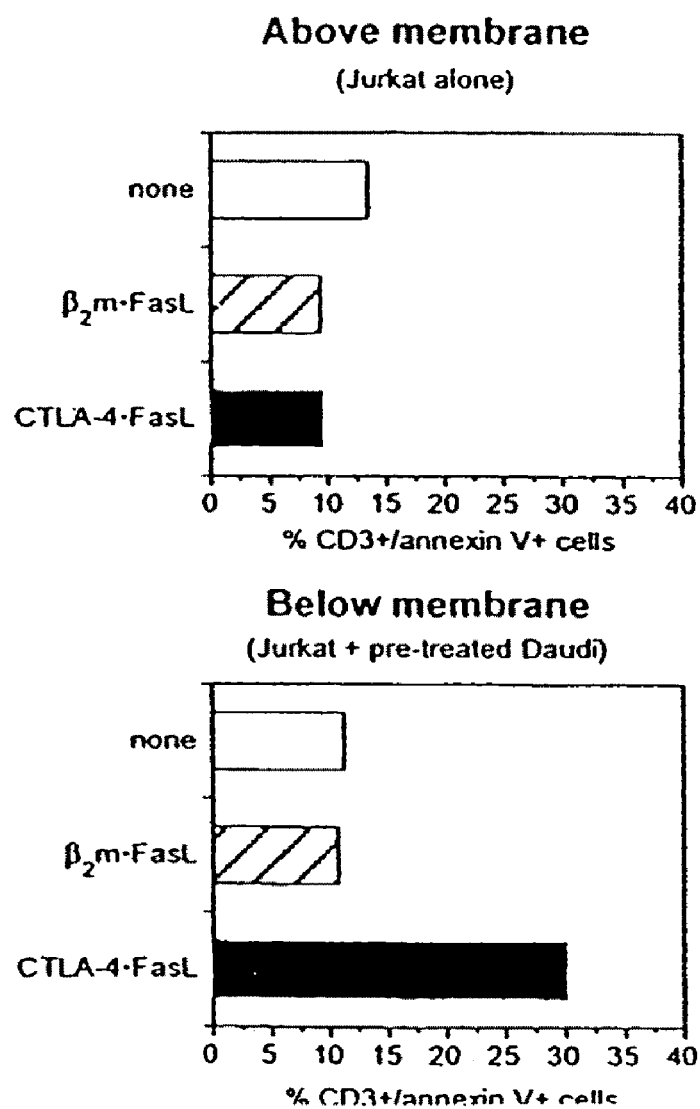

To determine whether cell-to-cell contact was required for the cytolytic effector function of CTLA-4•FasL-coated Daudi cells, membrane separation experiments were performed. Daudi cells were pre-incubated with medium alone, B2M•FasL or CTLA-4•FasL on ice for 1 hour. Following three washes, cells were counted and 0.25×10$^6$ and co-plated with 0.5×10$^6$ Jurkat cells beneath TRANSWELL™ semi-permeable membranes with a pore size of 3 microns in 24-well plates. 0.5×10$^6$ Jurkat cells were also added above the membranes. After 16 hours at 37° C., cells were harvested and processed for flow cytometry. Percentage of PI negative, CD3 bright, annexin V-bright events compared to total PI-negative, CD3-bright events are plotted on the x-axis in FIG. 2C. Following a 20 hour incubation, apoptosis of Jurkat cells was monitored by flow cytometric detection of bound fluorochrome-conjugated annexin V. Significant Jurkat cell PCD was observed only in the presence of Daudi cells coated with CTLA-4•FasL (FIG. 2C, lower panel). Addition of CTLA-4•FasL pre-treated Daudi cells below the membrane had no effect on the Jurkat cells harvested from above the membrane, consistent with a requirement for cell-cell contact (FIG. 2C, upper panel). As expected, no effect on Jurkat cell apoptosis was observed with control Daudi cells or B2M•FasL-pre-treated Daudi cells.

Example 3

Figure 3A:
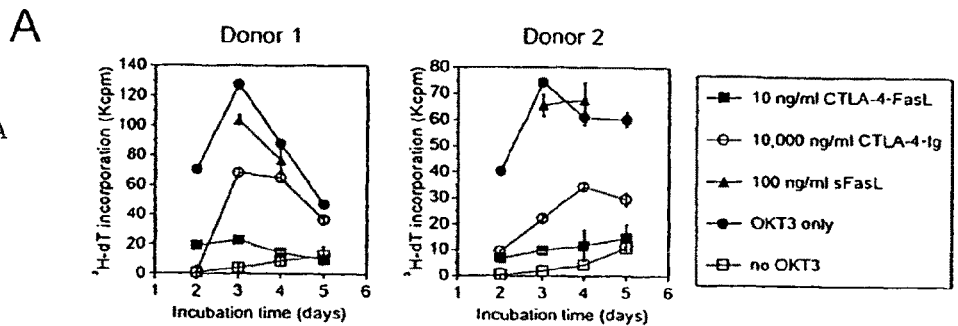
FIG. 3(A-C) demonstrates the dose-dependent inhibition of proliferation of human peripheral blood mononuclear cells, in response to anti-CD3 antibody stimulation, by CTLA-4•FasL, determined according to Example 3.
Figure 3B:
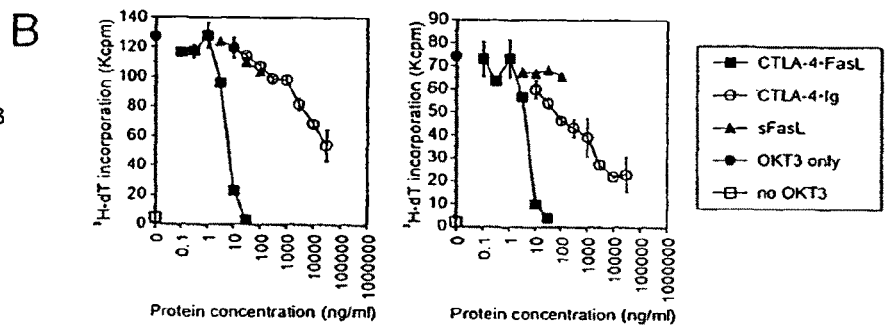
Figure 3C:
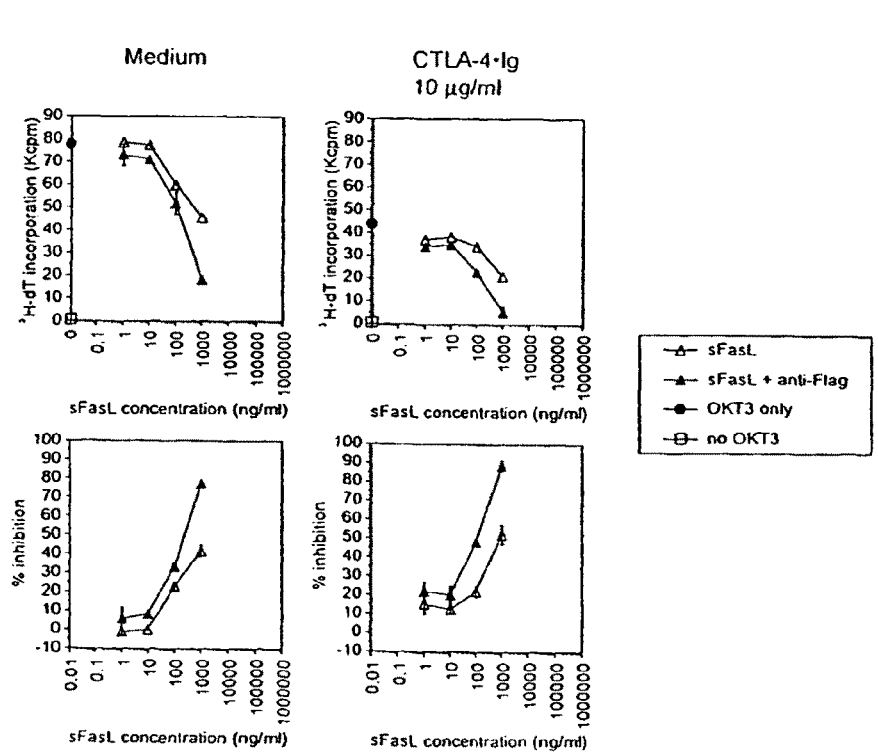

CTLA-4•FasL was tested for the capacity to inhibit the polyclonal proliferation of human peripheral blood T cells to mitogenic anti-CD3 antibody. In 96-well U bottom tissue culture plates, 2×10$^5$ PBMC/well of freshly isolated human peripheral blood mononuclear cells (PBMC) from two individual donors were cultured with 1 ng/ml CD3-specific antibody (OKT3) in the absence or presence of varying amounts of immunoaffinity-purified CTLA-4•FasL. Assays were performed in triplicate. Freshly isolated human peripheral blood mononuclear cells from two individual donors were cultured with 1 ng/ml CD3-specific antibody (OKT3) in the absence or presence of varying amounts of immunoaffinity-purified CTLA-4•FasL. For comparison, 10,000 ng/ml CTLA-4•Ig and recombinant human soluble FasL were also titrated into parallel cultures. After 36 hours and at 24-hour intervals for three additional days, culture wells were pulsed with $^3$H-thymidine to label the DNA of actively dividing T cells. 20 hours later, the radiolabeled DNA was harvested onto fiberglass filters and processed for scintillation counting. As can be seen in FIG. 3A, 10 ng/ml CTLA-4•FasL (filled squares) strongly inhibited the proliferation of human peripheral blood T cells stimulated by mitogenic anti-CD3 monoclonal antibody. For comparison, 10,000 ng/ml CTLA-4•Ig (open circles) inhibited proliferation by about 50% and 100 ng/ml sFasL (filled triangles) was minimally inhibitory. At the peak (day 3) of proliferation, inhibition of polyclonal T cell responses by varying amounts of CTLA-4•FasL, CTLA-4•Ig, sFasL was tested. As can be seen in FIG. 3B, CTLA-4•FasL (filled squares) was a significantly more potent inhibitor than either CTLA-4•Ig (open circles) or sFasL (filled triangles). Since antibody-mediated cross-linking of Flag-tagged, sFasL with Flag-epitope specific antibody, increased apoptosis of Fas-sensitive Jurkat cells, antibody cross-linking was tested for similar effect on the polyclonal proliferative response to anti-CD3. Hence, 0.5 µg/ml anti-Flag antibody was added in some assay wells along with varying amounts of sFasL. As can be seen in FIG. 3C (left panels), the inclusion of Flag-epitope specific antibody (sFasL+anti-Flag, filled triangles) increased inhibition only at the highest concentration (1,000 ng/ml) of sFasL tested in comparison to sFasL alone (open triangles). As can be seen in FIG. 3C, the combination of CTLA-4•Ig and sFasL (regardless of anti-Flag cross-linking) yielded additive effects on proliferative inhibition. Maximal inhibition required the combination of 10,000 ng/ml CTLA-4•Ig plus 1,000 ng/ml sFasL with anti-Flag antibody cross-linking. Thus, CTLA-4•FasL is more potent than either of its individual domain components, CTLA-4•Ig or sFasL, alone or in combination.

Example 4

Figure 4:
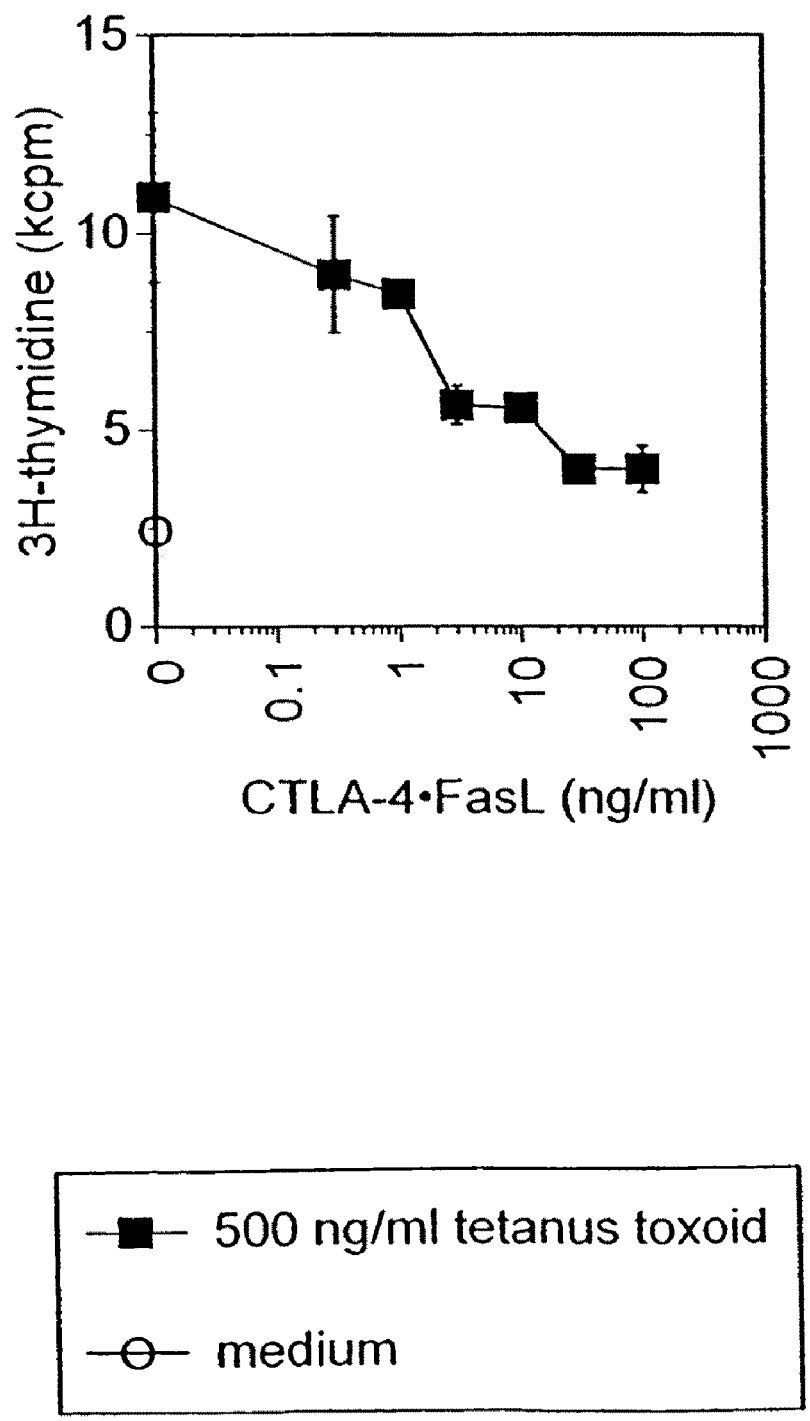
FIG. 4 demonstrates the ability of CTLA-4•FasL to inhibit an antigen-specific proliferative response to tetanus antigen, determined according to Example 4.

CTLA-4•FasL was tested for the capacity to inhibit the proliferation of human peripheral blood T cells in response to the specific antigen, tetanus toxoid. In 96-well U bottom tissue culture plates, $2 \times 10^5$ PBMC/well of freshly isolated human peripheral blood mononuclear cells (PBMC) were cultured with 500 ng/ml tetanus toxoid antigen in the presence or absence of varying amounts of immunoaffinity-purified CTLA-4•FasL. Assays were performed in triplicate. After 6 days, cultures were pulsed with $^3$H-thymidine to label the DNA of actively dividing T cells. 20 h later, the radiolabeled DNA was harvested onto fiberglass filters and processed for scintillation counting. As can be seen in FIG. 4, CTLA-4•FasL inhibited the proliferation of human peripheral blood T cells stimulated by the specific antigen, tetanus toxoid. Hence, CTLA-4•FasL is useful for inhibiting not just the polyclonal activation of T cells, but also T cell responses to specific antigens.

Example 5

Figure 5:
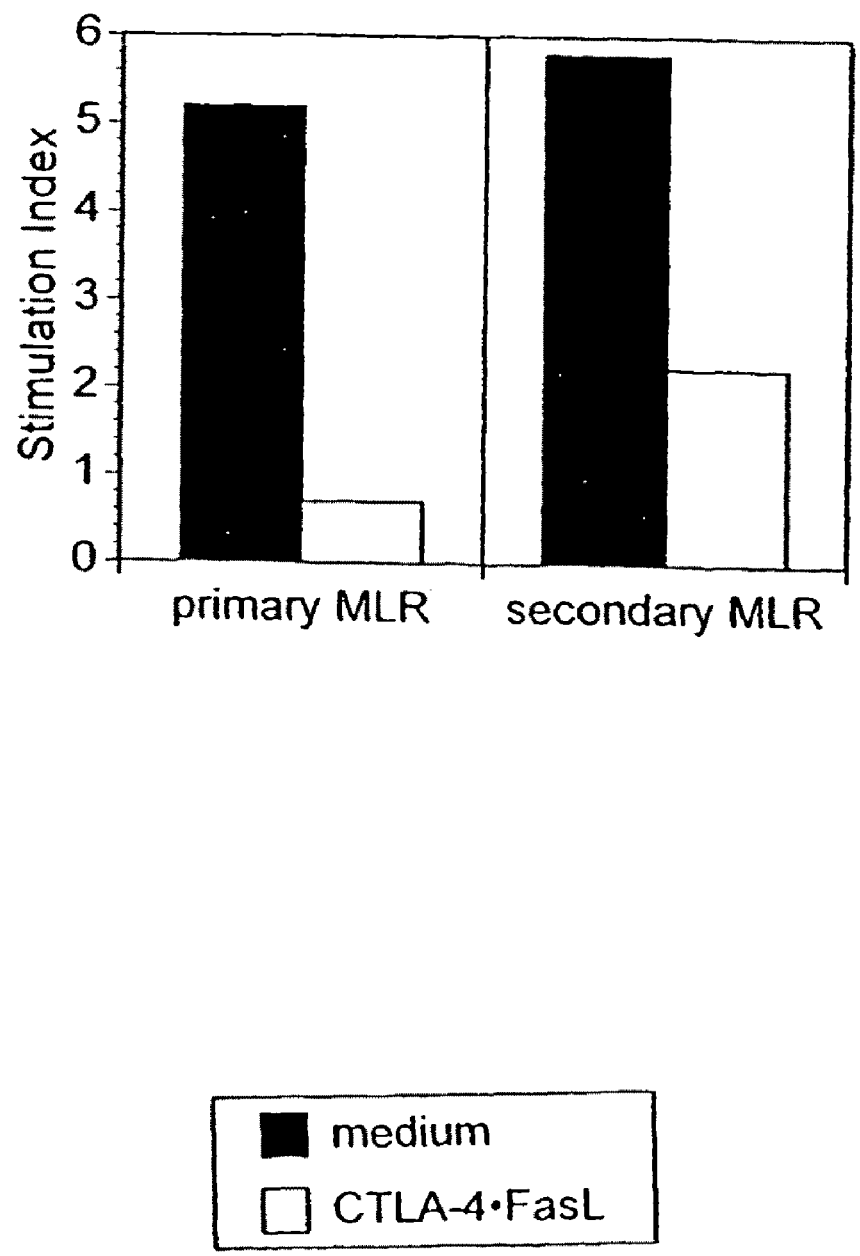
FIG. 5 demonstrates the ability of CTLA-4•FasL to inhibit specific proliferative responses to alloantigen in primary and secondary mixed lymphocyte co-culture, determined according to Example 5.

CTLA-4•FasL was tested for the capacity to inhibit the proliferative response of human peripheral blood T cells in response to alloantigen. In primary stimulation assays, alloantigen-presenting cells, the human Epstein-Barr virus-transformed human B lymphoblastoid cell line (EBV-LCL), were irradiated and added to cultures containing freshly purified human PBMC and 100 ng/ml CTLA-4•FasL. Assays were performed in triplicate in 96-well U bottom plates and contained $10^5$ PBMC and $2 \times 10^4$ irradiated EBV-LCL. Cultures were incubated for 4 days, and the T cell proliferative response to the EBV-LCL alloantigens was measured by pulsing with $^3$H-thymidine, harvesting the radiolabeled DNA onto fiberglass filters, and processing for scintillation counting. As can be seen in FIG. 5, the presence of CTLA-4•FasL, in comparison to medium alone, significantly reduced the primary alloantigen response of human peripheral T cells. In parallel with the primary stimulation assays, large-scale (10 ml) bulk cultures were performed in T25 flasks with the same proportions of peripheral blood mononuclear cells, irradiated EBV-LCL, and 30 ng/ml CTLA-4•FasL. After seven days, cells were harvested from the flasks, washed twice, and recultured in fresh medium, lacking CTLA-4•FasL for an additional 3 days. 10 days after the primary alloantigenic stimulations were initiated, cells were collected by centrifugation, washed twice, and replated in secondary stimulation assays in 96 well plates with irradiated EBV-LCL. Of note, no additional CTLA-4•FasL was added during these secondary stimulations. Similarly, as can be seen in FIG. 5, CTLA-4•FasL reduced the secondary response of human peripheral T cells to the same alloantigen. Thus, CTLA-4•FasL is useful for inhibiting both primary and secondary responses to alloantigen, which is significant for its therapeutic use to treat host-versus-graft and graft-versus-host alloantigenic T cells responses.

Example 6

Figure 6:
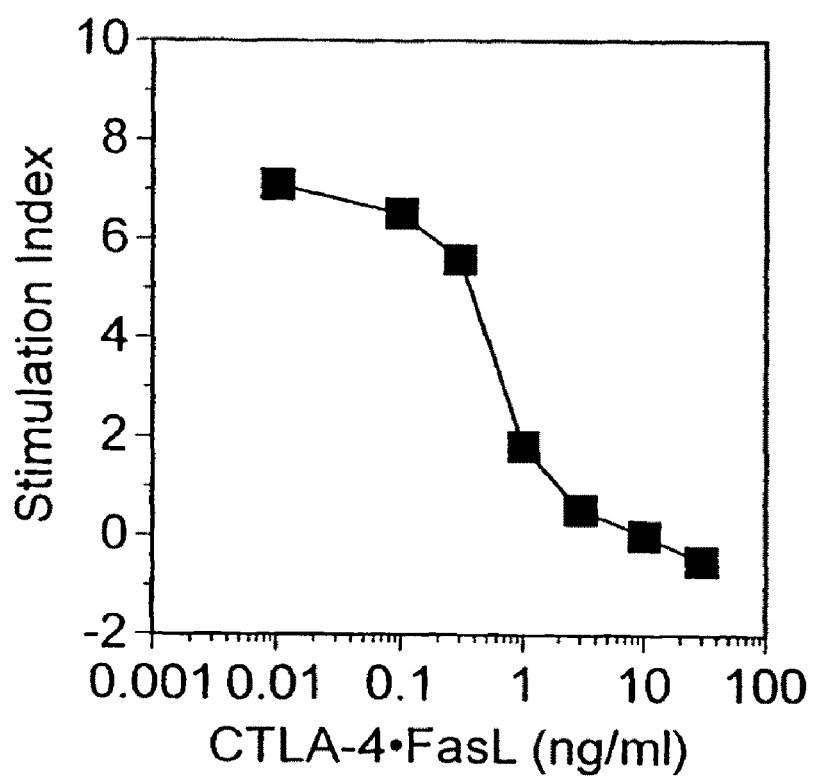
FIG. 6 demonstrates the ability of CTLA-4•FasL to inhibit Balb/c splenocyte proliferation in response to anti-CD3 antibody stimulation, determined according to Example 6.

Freshly isolated murine BALB/c splenocytes were cultured with mitogenic anti-CD3 antibody in the presence or absence of varying amounts of immunoaffinity-purified CTLA-4•FasL. Assays were performed in triplicate in 96-well U bottom plates and contained $2 \times 10^5$ splenocytes and 33 ng/ml anti-mouse CD3 antibody (2C11). After 24 hours, cultures were pulsed with $^3$H-thymidine to label the DNA of actively dividing T cells. 20 h later, the radiolabeled DNA was harvested onto fiberglass filters and processed for scintillation counting. As can be seen in FIG. 6, CTLA-4•FasL inhibits the proliferation of BALB/c T cells stimulated by anti-CD3 antibody, establishing that mouse T cells, just like human T cells, are susceptible to inhibition by CTLA-4•FasL.

Example 7

DNA primers for generating human TNF-related, apoptosis-inducing ligand (hTRAIL) cDNA sequence, encoding amino acids 95-281, were 5'-TAAAAAGCTTGAAAC-CATTTCTACAGTTCAA-3' (SEQ ID NO: 8) and 5'-TAAAGGATCCGGTCAGTTAGCCAACTAAAAA-3' (SEQ ID NO: 9). PCR was performed with Pfu DNA polymerase according to manufacturer's specifications, using the expressed sequence tag DNA subclone (ye16e08.r1, GenBank Acc: #T90422) known to encode the hTRAIL cDNA as a DNA template. Following purification and enzymatic restriction, the 564 bp HindIII-BamHI DNA fragment was subcloned into the respective sites of the episomal expression vector pCEP9β, generating pX•TRAIL/CEP9β. pCTLA-4•TRAIL/CEP9β was generated by subcloning the HindIII insert encoding the oncostatin M signal and human CTLA-4 extracellular sequences, together mobilized from phCTLA-4:IgG1/REP7β, into the HindIII site of pX•TRAIL/CEP9β.

DNA primers for generating human CD27 (hCD27) cDNA sequence, encoding amino acids −20-218, were 5'-TTTTG-GTACCATGGCACGGCCACATCC-3' (SEQ ID NO: 10) and 5'-GCACAAGCTTCTTTGGGGTGGCCAGTG-3' (SEQ ID NO: 11). PCR was performed with Pfu DNA polymerase according to manufacturer's specifications, using the expressed sequence tag DNA subclone (EST# yg25h11.r1, GenBank Acc# R25016.1) known to encode the hCD27 cDNA as a DNA template. Following purification and enzymatic restriction, the 652 bp KpnI-HindIII DNA fragment was subcloned into the respective sites of the episomal expression vector pX•TRAIL/CEP9β, generating pCD27•TRAIL/CEP9β.

Cell culture supernatants containing CD27•TRAIL or CTLA-4•TRAIL were obtained from stable transfectant cell lines derived by lipofection of the human embryonic kidney cell line, 293, with pCD27•TRAIL/CEP9β, or with pCTLA-4•TRAIL/CEP9β, respectively.

Figure 7:
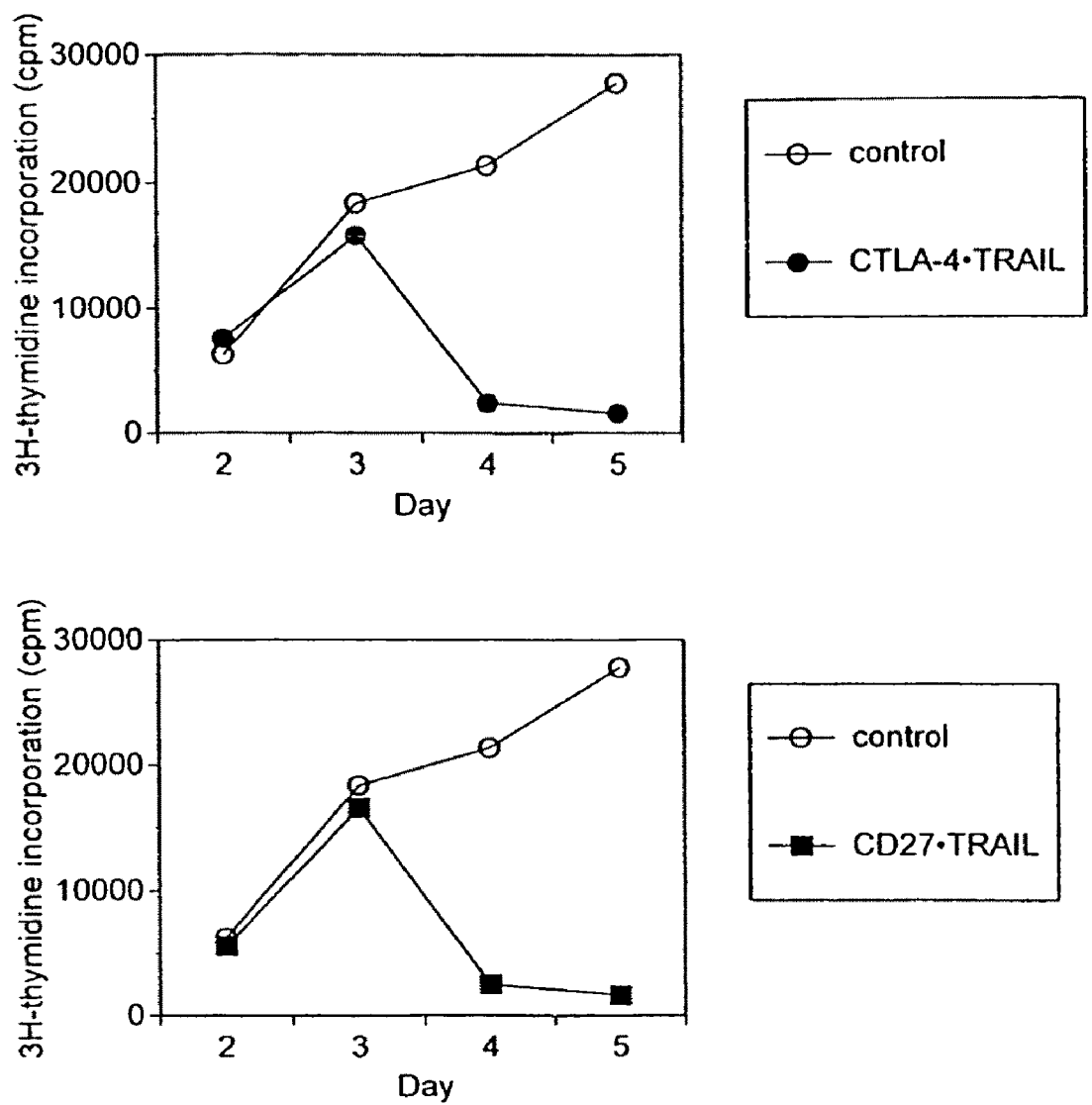
FIG. 7 demonstrates that inhibition of PBMC proliferation in response to anti-CD3 antibody stimulation by CTLA-4•TRAIL and CD27•TRAIL, determined according to Example 7.

Freshly isolated human PBMC were cultured with mitogenic anti-CD3 antibody, in the presence or absence of 1:300 (v/v) diluted CD27•TRAIL- or CTLA-4•TRAIL-conditioned cell culture supernatant. Assays were performed in triplicate in 96-well U bottom plates and contained $2 \times 10^5$ PBMC and 0.3 ng/ml anti-CD3 (OKT3). After 24 hours, and every 24 hours thereafter for 3 additional days, cultures were pulsed with $^3$H-thymidine to label the DNA of actively dividing T cells. 20 hours later, the radiolabeled DNA was harvested onto fiberglass filters and processed for scintillation counting. As can be seen in FIG. 7, both CD27•TRAIL and CTLA-4•TRAIL strongly inhibited anti-CD3 antibody-stimulated proliferation of human peripheral T cells after day 3. These data introduce two additional examples of chimeric proteins (CD27•TRAIL and CTLA-4•TRAIL), which serve to further illustrate the generality of the concept of the chimeric proteins of the present invention. Moreover, they demonstrate how the present invention enables the rapid design, production and evaluation of additional functional chimeric proteins.

As shown in Examples 1-3, significant Jurkat cell PCD was observed with the addition of 0.1 ng/ml of CTLA-4•FasL in the presence of Daudi cells. At higher concentrations of soluble CTLA-4•FasL, no cross-linking cells were necessary for the induction of Jurkat cell apoptosis. These observations contrast with B2M•FasL, which displayed no significant cytocidal effects in the absence of cross-linking antibody. Examples 4 and 5 extend the findings of Examples 1-3, going beyond polyclonal T cell activators to demonstrate that CTLA-4•FasL inhibits specific T cell responses, either to specific antigen (Example 4) or specific alloantigen (Example 5). Example 6 further shows that human CTLA-4•FasL inhibits murine T cell responders.

Examples 1-4 also demonstrate that use of a targeting domain sequence as the first protein, namely, the CTLA-4 ectodomain, directs the binding of sFasL to cell surface CD80/CD86 target molecules. Thus, this demonstrates the efficacy of using the amino terminal domain of a chimeric protein for the purpose of cell surface molecular targeting and the use of a type II membrane protein derivative as a second protein component within a chimeric protein. This also demonstrates the generation of a novel chimeric protein, CTLA-4•FasL, that mediates costimulation blockage and FasL transeffector activity when bound to APC. This cell-based modification can be used to convert stimulatory APC to immunoinhibitory APC by simultaneously blocking costimulator molecules and presenting inhibitory molecules.

Similar results are demonstrated in Example 7 wherein two additional chimeric proteins, namely CTLA-4•TRAIL and CD27•TRAIL, have been shown to bind to APC and send inhibitory trans signals. These findings establish the generality of the novel chimeric proteins of the present invention, with no undue experimentation required to add to the series of functional proteins in this class.

These above examples establish that the soluble, chimeric proteins of the present invention display binding and functional properties derived from the individual domains. Moreover, the data indicate that soluble chimeric mediators are useful for therapeutic targeting of pathogenic T cells for programmed cell death.

Whereas particular embodiments of this invention have been described above for purposes of illustration, it will be evident to those skilled in the art that numerous variations of the details of the present invention may be made without departing from the invention as defined in the appended claims.

What is claimed is:

1. A chimeric protein comprising:

a first protein that binds to at least one surface molecule on a first cell and results in the decrement of a first trans signal from said cell; and a second protein that binds to at least one surface molecule on a second cell and sends a second trans signal to said second cell, wherein the first and second trans signals sent from the surface of said first and second cells are not the same, and wherein when the first protein is selected from the group consisting of CTLA-4, CD27, CD40, and ICOS and second protein is selected from the group consisting of FasL, TRAIL, TWEAK, CAR, CD8, PP14, BAFF/TALL-1/THANK/BLys, PD-1 and RCAS1.

2. The chimeric protein of claim 1, wherein said first protein is CTLA-4 and said second protein is FasL.

3. A pharmaceutical formulation comprising the chimeric protein of claim 1 or 2 in a suitable pharmaceutical carrier, wherein said pharmaceutical formulation is administered in unit dosage form to a patient in need thereof in therapeutically effective amounts.

* * * * *